United States Patent [19]

Copp et al.

[11] 4,414,223
[45] Nov. 8, 1983

[54] PESTICIDAL ANILINOMETHYLIMIDAZOLINES

[75] Inventors: Frederick C. Copp, Beckenham; Peter T. Roberts, Berkhamsted; Alexander D. Frenkel, Aston Clinton; David Collard, Beckenham, all of England

[73] Assignee: Burroughs Wellcome Co., Research Triangle Park, N.C.

[21] Appl. No.: 264,305

[22] Filed: May 18, 1981

Related U.S. Application Data

[60] Continuation of Ser. No. 52,860, Jun. 28, 1979, abandoned, which is a division of Ser. No. 862,169, Dec. 19, 1977, abandoned.

[30] Foreign Application Priority Data

Dec. 20, 1976 [GB] United Kingdom ............... 53059/76
Dec. 20, 1976 [GB] United Kingdom ............... 53061/76
Dec. 20, 1976 [GB] United Kingdom ............... 53062/76

[51] Int. Cl.$^3$ ............................................. A01N 43/50
[52] U.S. Cl. ................................. 424/273 R; 548/353
[58] Field of Search ..................... 424/273 R; 548/353

[56] References Cited

FOREIGN PATENT DOCUMENTS 51-106739 9/1976 Japan .
76-1508 11/1976 South Africa .

*Primary Examiner*—Richard A. Schwartz
*Attorney, Agent, or Firm*—Donald Brown

[57] ABSTRACT

1-Phenoxyalkyl- and 1-anilinoalkyl imidazolines, methods for the preparation thereof, the use thereof as intermediates and pesticides and pesticidal formulations containing such compounds.

5 Claims, No Drawings

PESTICIDAL ANILINOMETHYLIMIDAZOLINES

This is a continuation, of application Ser. No. 052,860 filed June 28, 1979, now abandoned, which is a division of application Ser. No. 862,169 filed Dec. 19, 1977, now abandoned.

This invention relates to imidazolines, their preparation, pesticidal formulations containing them and to their use as pesticides.

The invention in one aspect provides a pesticidal formulation comprising, as active ingredient, at least one compound of formula (I):

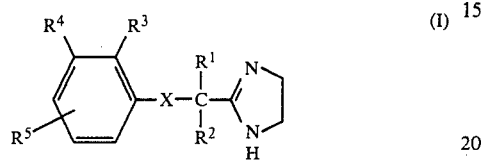

wherein
$R^1$ and $R^2$ are the same or different and are hydrogen or alkyl;
X is O or NH;
$R^3$ and $R^4$ are the same or different and are hydrogen, alkyl, alkoxy, halogen, hydroxy, cyano or trifluoromethyl or $R^3$ and $R^4$ together may form a polymethylene chain of 3 or 4 carbon atoms; and
$R^5$ is hydrogen, alkyl, alkoxy, halogen, hydroxy, cyano, nitro, hydroxy or methanesulphonamido in one of the 4, 5 or 6 positions; provided that:
at least one of $R^3$, $R^4$ and $R^5$ is other than hydrogen;
when any two of $R^3$, $R^4$ and $R^5$ are hydrogen the remaining group is not alkyl, halogen, nitro or trifluoromethyl;
when one of $R^3$ and $R^4$ is hydrogen and one of $R^5$ and the remaining group ($R^3$ or $R^4$) is alkyl, halogen, nitro or trifluoromethyl, then the other group is not alkyl, halogen, nitro or trifluoromethyl;
when at least one of $R^1$ and $R^2$ is alkyl and $R^5$ is hydrogen then at least one of $R^3$ and $R^4$ is cyano, alkoxy or hydroxy;
when $R^1$, $R^2$ and $R^5$ are all hydrogen then at least one of $R^3$ and $R^4$ is hydroxy, alkoxy or cyano or $R^3$ is methyl or chloro and $R^4$ is chloro;
when none of $R^3$, $R^4$ and $R^5$ is hydrogen at least one of them is other than alkyl, nitro, halogen or trifluoromethyl, or an acid addition salt thereof.

In a second aspect the invention provides substituted phenoxyalkyl and anilinoalkylimidazolines of formula (II) below and acid addition salts thereof.
Compounds of formula (II) are:

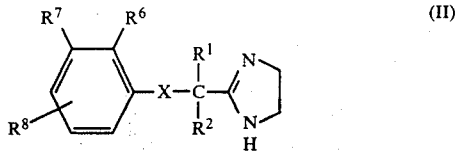

wherein
$R^1$, $R^2$ and X are as defined in formula (I) above;
$R^6$ and $R^7$ are the same or different and are hydrogen, alkyl, alkoxy, halogen hydroxy, cyano or trifluoromethyl or $R^6$ and $R^7$ together may form a polymethylene chain of 3 or 4 carbon atoms; and
$R^8$ is hydrogen, alkyl, alkoxy, halogen, cyano, nitro, hydroxy or methanesulphonamido in one of the 4, 5 or 6 positions; provided that:
at least one of $R^6$, $R^7$ and $R^8$ is other than hydrogen;
when any two of $R^6$, $R^7$ and $R^8$ are hydrogen the remaining group is not alkyl, alkoxy, halogen, hydroxy, nitro or trifluoromethyl except that when $R^1$, $R^2$, $R^5$ and $R^6$ are all hydrogen, $R^8$ may be ethoxy;
when one of $R^6$ and $R^7$ is hydrogen, $R^8$ and the remaining group ($R^6$ or $R^7$) are different unless both are cyano or hydroxy;
when one of $R^6$ and $R^7$ is hydrogen and one of $R^8$ and the remaining group ($R^6$ or $R^7$) is alkyl, halogen, nitro or trifluoromethyl then the other group is not alkyl, halogen, nitro or trifluoromethyl;
when one of $R^6$ and $R^7$ is hydrogen and one of $R^8$ and the remaining group ($R^6$ or $R^7$) is halogen the other is not alkoxy;
when at least one of $R^1$ and $R^2$ is alkyl and $R^8$ is hydrogen then at least one of $R^6$ and $R^7$ is cyano or hydroxy;
when $R^1$, $R^2$ and $R^8$ are all hydrogen, either at least one of $R^5$ and $R^6$ is cyano or hydroxy or $R^6$ is methyl methoxy or chloro and $R^7$ is methyl;
when none of $R^6$, $R^7$ and $R^8$ are hydrogen at least one of them is other than alkyl, halogen, nitro or trifluoromethyl.

As used herein, halogen includes chloro, fluoro and bromo, and the alkyl and alkoxy groups and moieties each have 1 to 4 carbon atoms.

The compounds of formula (I) and formula (II) (which are within the scope of formula (I)) and their acid addition salts have activity against arthropods, in particular against members of the Order Acarina. In particular, they have been found active against *Rhipicephalus appendiculatus, Boophilus docoloratus* and *Boophilus microplus*. The compounds of formula (I) and formula (II) and their acid addition salts may therefore be used to contaol these pests, or other arthropod pests such as *Rhipicephalus evertsi, Amblyomma hebracum, Psoroptes ovis* and Hyalomma species on aminals and Tetranychus species on plants.

Japanese Patent Publication No. 76/106739 discloses compounds of the general formula

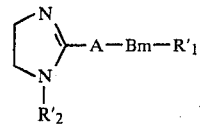

wherein
A is lower alkylene or alknylene;
B is O, S, NH or $NCH_3$;
m is 0 or 1;
$R'_1$ is phenyl; mono- di- or tris-substituted phenyl wherein the substituents are selected from halogen, nitro, lower alkyl, halo-(lower alkyl); thienyl or naphthyl; and
$R'_2$ is H or lower alkyl,
and insecticidal and acaricidal formulations containing such compounds.

We have found that compounds of formula (II) wherein $R^1$, $R^2$ and $R^8$ are hydrogen, X is O or NH, $R^3$ is methyl or chloro and $R^4$ is methyl (and hence also compounds of formula (I) wherein $R^1$, $R^2$ and $R^5$ are hydrogen, X is O or NH, $R^3$ is methyl or chloro and $R^4$ is methyl) are advantageous with respect to their acaricidal activity and/or mammalian toxicity over compounds specifically disclosed in Japanese Patent Publication No. 76/106739.

Compounds of formula (I) and formula (II) are also of value as intermediates in the preparation of compounds of formula (III) below which have utility as acaricides:

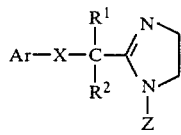
(III)

wherein $R^1$, $R^2$ and X are as defined in formula (I) above,

Ar is an unsubstituted or mono-, di or tri-substituted phenyl radical in which the substituents are the same or different and are selected from alkyl, alkoxy, halogen, hydroxy, cyano, amino, trifluoromethyl or nitro and in which any two adjacent carbon atoms on the phenyl ring may optionally be joined by a carbon chain having 3 or 4 carbon atoms; and Z is a group $SO_nR^9$ or a group

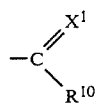

in which $X^1$ is O, S or $NR^{11}$;

$R^{10}$ is alkyl, aryl, alkyloxy, aryloxy or $NR^{12}R^{13}$;

$R^{11}$ is alkyl, aryl, alkyloxy, aryloxy, alkylthio, arylthio or $NR^{12}R^{13}$;

$R^{12}$ and $R^{13}$ are the same or different and are hydrogen, alkyl, aryl, $COR^{14}$ or $SO_2R^{14}$;

$R^{14}$ is alkyl, aryl, alkyloxy or aryloxy; n is 1 or 2;

$R^9$ is alkyl, aryl or $NR^{15}R^{16}$; and $R^{15}$ and $R^{16}$ are the same or different and are hydrogen, alkyl or aryl.

Of particular interest, both as highly active compounds and as intermediates to compounds of formula (III), are compounds of formula (I) wherein $R^1$, $R^2$ and X are as defined above, $R^5$ is H, $R^4$ is methyl and $R^3$ is methyl or chloro.

Particularly valuable compounds are:
2-(2,3-dimethylphenoxymethyl)-2-imidazoline;
2-(2,3-dimethylanilinomethyl)-2-imidazoline; and
2-(2-chloro-3-methylanilinomethyl)-2-imidazoline.

The compounds of formula (I) and formula (II) and their acid addition salts may be prepared by any known method for the preparation of compounds of analogous structure.

In particular compounds of formula (II) may be prepared by reacting ethylenediamine with an appropriate phenoxyalkyl or anilinoalkyl carboxylic acid or derivative thereof, which compounds may be represented by the formula (IV):

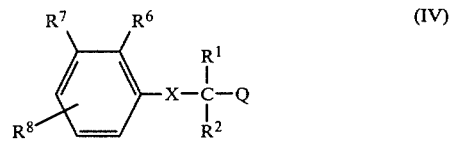

wherein $R^1$, $R^2$, $R^6$, $R^7$, $R^8$ and X are as defined in formula (II) above, and Q is a carboxyl group or a reactive derivative thereof which produces an imidazoline ring structure of formula (II) when reacted with ethylene diazine.

Q in formula (IV) may suitably be:

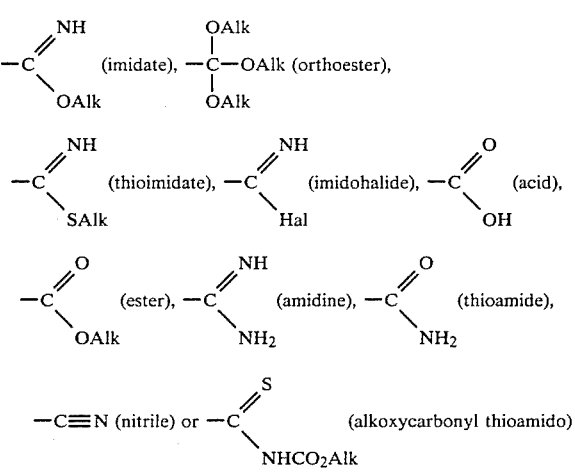

wherein 'Alk' is an alkyl group having 1 to 6 carbon atoms.

The conditions under which this reaction may be carried out of course depends upon the nature of the starting materials used, and a liquid medium may be present or absent; high and low temperatures may be used, and various pressures employed.

When the carboxylic acid derivative is an imidate, this is preferably in the form of an acid addition salt such as a hydrogen halide salt, and may be prepared from the nitrile and a suitable anhydrous alkanol such as ethanol or methanol in the presence of dry diethylether or chloroform and hydrogen chloride at a low temperature. The reaction may be carried out at a temperature in the range of $-20°$ C. to ambient temperature. The reaction with ethylenediamine is conducted in an inert anhydrous medium such as chloroform, methylene chloride or ether. The reactants are preferably heated under reflux until reaction is complete.

The thioimidate intermediates in the form of acid addition salts may be prepared from the corresponding nitrile by reaction with an alkyl mercaptan and a hydrogen halide gas at low temperatures about $0°$ C., in the presence of dry diethyl ether. The thioimidates may then be reacted with ethylenediamine in the presence of a hydrogen halide acceptor by heating to the reflux temperature of the reaction mixture.

The ester intermediates may be conveniently prepared from the corresponding acid by known methods, and the acid itself may be prepared from the corresponding nitrile. They may then be reacted with ethylenediamine, preferably in the presence of a liquid medium which may be polar or non-polar. The reaction is preferably effected at elevated temperature.

The compounds of formula (II) may be prepared from the imidohalide intermediates by reaction with ethylenediamine under anhydrous conditions in the presence or absence of an acid acceptor and optionally at an elevated temperature. The reaction mixture may include a polar or non-polar liquid medium such as a lower alkanol or an ether.

The amidine intermediate in the form of the base or acid addition salts thereof, is preferably converted to a compound of formula (II) by heating under reflux with ethylenediamine in the presence of a polar or non-polar liquid medium, for example a lower alkanol, until ammonia ceases to be evolved. Alternatively, ethylene dichloride or 2-chloroethylamine may be used in place of ethylenediamine. The amidine intermediates themselves may be prepared by any known method, but conveniently from the corresponding imidates by reaction with ammonia.

The thioamide intermediates may be prepared from the corresponding nitriles or by any other convenient method and may be converted into compounds of formula (II) by heating with ethylenediamine at a reflux or higher temperature, in the presence or absence of a polar or non-polar solvent. Conveniently the reactions are partly effected under reduced pressure to induce the removal of ammonia and/or hydrogen sulphide from the reaction mixture.

The nitrile intermediates are reacted in the presence or absence of a liquid medium with ethylenediamine or a salt thereof; the reaction may be carried out in the presence of hydrogen sulphide. A liquid medium such as a lower alkanol may be included in the reaction mixture which may be heated to a reflux temperature, or to a higher temperature in a closed vessel, optionally in the presence of an inert gas such as nitrogen.

It will of course be understood that where the intermediate is the carboxylic acid, ester, or thioamide, there may be isolated as an intermediate the acylethylenediamines of formula (V)

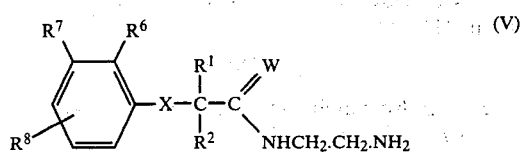

wherein $R^1$, $R^2$, $R^6$, $R^7$, $R^8$ and X are as defined above and W is oxygen or sulphur and these compounds may themselves be converted in situ to a compound of formula (II), either by separate treatment with a dehydrating agent such as calcium oxide or by continuing the reaction to completion under the original conditions giving rise to a compound of formula (II).

The compounds of formula (II) may also be prepared by the reaction of a phenol or amine of formula (VI) or an O- or N-metal salt thereof

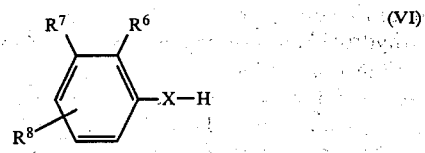

wherein $R^6$, $R^7$, $R^8$ and X are as defined in formula (I) above with a reactive ester, derivative of formula (VII)

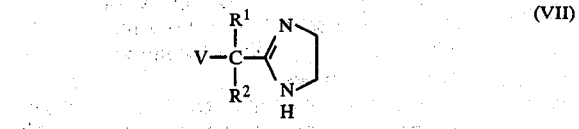

wherein $R^1$ and $R^2$ are as defined in formula (II) above and V is a leaving group derived from a suitable inorganic or organic acid. Suitable derivatives are halo, such as chlor, iodo, or bromo, alkylsulphonyloxy or arylsulphonyloxy such as p-toluenesulphonyloxy.

The reactive ester derivatives of formula (VIII) may be in the form of their bases or acid addition salts thereof. The reaction is carried out in an inert medium which is preferably a polar liquid such as acetonitrile or isopropanol, or may be dimethylsulphoxide, sulpholane, methyl ethyl ketone, dimethylformamide, acetone, dimethylacetamide, N-methyl-2-pyrrolidone, or mixtures of the foregoing. In the case where V is chloro in a compound of formula (VIII), then a small catalytic quantity of an iodide salt for example sodium iodide, or a phase transfer catalyst such as a quaternary ammonium salt such as benzyltrimethylammonium chloride may advantageously be included in the reaction mixture. The reactants may be heated together under an inert atmosphere such as nitrogen at the reflux temperature of the reaction mixture.

The compounds of formula (II) may be isolated from the reaction mixture as the free base or in the form of an acid addition salt. The bases may be converted into acid addition salts thereof by known techniques with the aid of the appropriate acid, and salts of the compound may also be converted into the free bases or into other acid addition salts.

For use as a pesticide, the compounds of formulae (I) and (II) may be presented in the form of their free bases, or as acid addition salts thereof. Suitable salts of formulae (I) and (II) include hydrohalide, sulphate, nitrate, phosphate, thiocyanate, acetate, proionate, naphthenate, perchlorate, benzoate, methanesulphonate, ethanesulphonate, tosylate and benzenesulphonate acid addition salts thereof.

The compounds of formula (I) may be used as pesticides against insects, ticks and other arthropods including free living arthropods and those which are ectoparasites of mammals, and may be used alone or in combination with a carrier which may take the form of one or more of the following: wetting, diluent, stabilising, thickening, emulsifying, dispersing or surface active agents or other standard carrier ingredients.

A formulation may be an aqueous solution of an acid addition salt of a compound of formula (I), or a suspension of a compound of formula (I) in water, and may be used alone or in combination with suitable surface active agents. The formulation per se may be used alone or diluted in water for application to the pests or their immediate environment by way of spraying or dipping.

A formulation may be in the form of a miscible oil comprising a compound of formula (I) in the form of its free base and an equimolar quantity of a suitable organic acid, such as naphthenic acid, to provide a salt soluble in organic solvents, and emulsifiers, and are applied as an emulsion in water by way of spraying or dipping.

A formulation may be a non-aqueous solution or suspension of a compound of formula (I) in a suitable organic solvent for the direct application by the "pour-on" method.

A formulation may also take the form of a wettable powder for diultion with water and application by dipping or spraying. Other solid formulations may also be used for direct application without dilution, such as dusts, powders and granules.

A further formulation may be a paste, grease or gel, containing a compound of formula (I) and a suitable carrier, and may be applied by spreading the formulation over the infected area.

An acid addition salt or base of a compound of formula (I) is preferably present in a pesticidal formulation in an amount between 5 and 80%, calculated by weight of the base, and particularly preferred formulations contain about 20%, calculated by weight of the base.

The concentration of a compound of formula (I) applied to the pests or their immediate environment may be in the range of 0.001%–20%, calculated by weight of the base.

It will be appreciated from the foregoing that what we will claim may comprise any novel feature described herein, principally and not exclusively, for example:

(a) A novel substituted alkylimidazoline compound of formula (II) or an acid addition salt thereof;
(b) A method of preparation of a novel compound of formula (II) or an acid addition salt thereof;
(c) A method of controlling arthropod pests, particularly members of the class Insecta and the order Acarina, by applying to the pest or the pest's environment a compound of formula (I) or an acid addition salt thereof;
(d) A pesticidal formulation comprising a compound of formula (I) or an acid addition salt thereof and a carrier therefor;
(e) A method of making a formulation comprising an admixture of a carrier and a compound of formula (I) or an acid addition salt thereof;

The following Examples are provided by way of an illustration of the present invention and should not be construed as in any way constituting a limitation thereof. All temperatures are in degrees Celsius.

EXAMPLE 1

2-(2,3-Dimethylanilinomethyl)-2-imidazoline hydriodide

2-Chloromethyl-2-imidazoline hydrochloride (4 g), 2,3-dimethylaniline (6.24 g) and phenol (2 g) were stirred together at 140° C. in an atmosphere of nitrogen. After 15 minutes a semi-solid mass had been formed which was allowed to cool after a further 15 minutes. Water (70 ml) was added to the mixture and the phenol was removed with ether. The aqueous residue was treated with aqueous 2 N-sodium hydroxide (11 ml), extracted twice with ether to remove the excess 2,3-dimethylaniline and the aqueous solution was evaporated in vacuo. The solid residue was re-dissolved in water (50 ml) and solid potassium iodide (10 g) added to precipitate 2-(2,3-dimethylanilinomethyl)-2-imidazoline hydriodide. It crystallised from isopropanol as colourless prisms, m.p. 221°–222° C.

EXAMPLE 2

Preparation of hydrochloride acid addition salt of the imidazoline of Example 1

The hydriodide from Example 1 (1 g) was dissolved in cold water (100 ml); a large excess of aqueous sodium hydroxide (10 N; 15 ml) was added and the solution was extracted three times with ether. The combined extracts were dried over anhydrous potassium carbonate, filtered and evaporated. The residual base was an oil (600 mg). It was dissolved in a slight excess of 2 N hydrochloric acid and evaporated. The resulting 2-(2,3-dimethylanilinomethyl)-2-imidazoline hydrochloride was recrystallised from ethanol, m.p. 236°–237° C.

EXAMPLE 3

2-(2-Chloro-3-methylanilinomethyl)-2-imidazoline hydrochloride 2-(2-Chloro-3-methylanilinomethyl)-2-imidazoline was prepared by the method described in Example 1, from 2-chloromethyl-2-imidazoline hydrochloride and 2-chloro-3-methyl aniline (m.p. 248°–249° C.).

EXAMPLES 4-11

The foregoing Examples were prepared by methods analogous to that of Example 1.

EXAMPLE 4

2-(2-Cyano-3-methylanilinomethyl)-2-imidazoline hydrochloride (m.p. 234°–235° C.).

EXAMPLE 5

2-(2-Methoxy-3-methylanilinomethyl)-2-imidazoline hydrochloride (m.p. 183°–184° C.).

EXAMPLE 6

2-(4-Methoxyanilinomethyl)-2-imidazoline hydrochloride (m.p. 160°–162° C.).

EXAMPLE 7

2-(4-Methanesulphonamidoanilinomethyl)-2-imidazoline (m.p. 215°–217° C.).

EXAMPLE 8

2-(2-Isopropoxy-3-methylanilinomethyl)-2-imidazoline hydrochloride (m.p. 201°–202° C.).

EXAMPLE 9

2-(4-Cyanoanilinomethyl)-2-imidazoline hydriodide (m.p. 211°–213° C.).

EXAMPLE 10

2-(3-Hydroxyanilinomethyl)-2-imidazoline hydriodide (m.p. 184°–185° C.).

EXAMPLE II 2-(5-Hydroxyanilinomethyl)-2-imidazoline hydrochloride (m.p. 180°–181° C.).

EXAMPLE 12

2-(4-Ethoxyphenoxymethyl)-2-imidazoline hydrogen tosylate

Metallic sodium (2.29 g; 0.10 moles) was dissolved in absolute ethanol (30 moles) containing 4-ethoxyphenol (6.9 g; 0.05 moles). A solution of 2-(chloromethyl)-2-imidazoline hydrochloride (7.71 g; 0.05 moles) (which can readily be prepared from ethyl chloroacetimidate hydrochloride and ethylenediamine) in absolute ethanol (20 ml) was added dropwise. The mixture was then refluxed for 2½ hours. After cooling the bulk of the solvent was removed and the residue was extracted into chloroform/water. This extract was washed with water, dried over magnesium sulphate, the solvent then removed and the residue dissolved in cold diethylether from which the 2-(4-ethoxyphenoxymethyl)-2-imidazoline hydrogen tosylate was precipitated by the addition of toluene-p-sulphonic acid. The product was recrystallised from ethanol, m.p. 180°–182° C.

EXAMPLES 13–15

The following Examples were prepared by a method analogous to that of Example 12.

EXAMPLE 13

2-(2,3-Dimethylphenoxymethyl)-2-imidazoline (m.p. 121°–123° C.).

EXAMPLE 14

2-(2,3-Dimethylphenoxymethyl)-2-imidazoline hydrochloride 0.33 hydrate (m.p. 200° C. dec.).

EXAMPLE 15

2-(4-Indanyloxymethyl)-2-imidazoline hydrochloride (m.p. 249°–250° C. dec.).

EXAMPLE 16

In vitro tests on *Boophilus decoloratus ACR*, (arsenic and chlorinated hydrocarbon cross resistant strain) and *Boophilus microplus OP*, (organophosphorus resistant strain). In the results tabulated below LC 99% indicates the concentration of active compound lethal to 99% of the larval population, and IR 90% indicates the concentration which inhibits 90% of the engorged adult females from producing viable eggs.

| Compound | Example No. | B. doc. (ACR) LC 99% | IR 90% | B. microplus (OP) LC 99% | IR 90% |
|---|---|---|---|---|---|
| 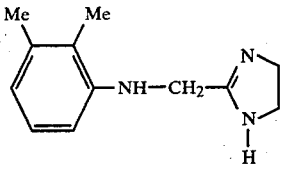 | 1 | <0.005 | <0.02 | <0.005 | <0.02 |
| 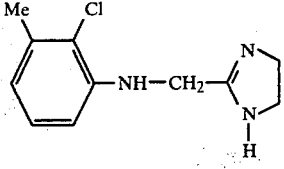 | 3 | <0.00001 | <0.01 | <0.00001 | <0.01 |
| 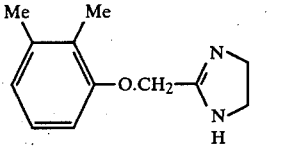 | 13 | <0.001 | — | <0.00015 | <0.0021 |

The following formulation are given to illustrate the way in which the pesticidal compounds of the invention can be applied to pests or environments susceptible to pest attack.

FORMULATION 1

Dusting Powders

| Active Compound | 1.0 | 20.0 parts by wt. |
| Kaolin or Talc | 99.0 | 80.0 parts by wt. |
| | 100.0 | 100.0 |

FORMULATION 2

Wettable Powder

| Active Compound | 25.0 parts by wt. |
| Sodium Dioctyl Sulphosuccinate | 1.2 parts by wt. |
| Dispersol ACA | 3.0 parts by wt. |
| Kaolin | 70.8 parts by wt. |
| | 100.0 |

FORMULATION 3

Soluble Powders

| Active Compound (as soluble acid addition salt) | 75.0 parts by wt. |
| Sodium Xylene Sulphonate | 2.0 parts by wt. |
| Sodium Dioctyl Sulphosuccinate | 5.0 parts by wt. |
| Sodium Sulphate | 18.0 parts by wt. |
| | 100.0 |

FORMULATION 4

Aqueous Solution

| Active Compound (as soluble acid addition salt) | 10.0 parts by wt. |
| Nonyl Phenol Ethoxylate | 1.0 parts by wt. |
| Water | 89.0 parts by wt. |
| | 100.0 |

FORMULATION 5

Grease

| Active Compound | 10.0 parts by wt. |
| Petroleum Jelly | 90.0 parts by wt. |
| | 100.0 |

FORMULATION 6

Miscible Oil

| | |
|---|---|
| Active Compound | 12.0 parts by wt. |
| Naphthenic Acid | 26.0 parts by wt. |
| Nonyl Phenol Ethoxylate | 20.0 parts by wt. |
| Esso Solvent 200 | 42.0 parts by wt. |
| | 100.0 |

We claim:

1. A method for preventing pests of the Order Acarina from producing viable eggs which comprises applying to the pest or the pest's environment an effective amount of a compound of formula (I)

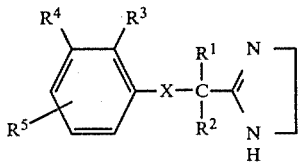

wherein
$R^1$ and $R^2$ are hydrogen;
X is NH
$R^3$ and $R^4$ are the same or different and are methyl or chloro;
and $R^5$ is hydrogen or an acid addition salt thereof to inhibit the production of viable eggs by said pests.

2. A method as claimed in claim 1 wherein the pests are ticks.

3. The method of claim 1 in which 2-(2,3-dimethylanilinomethyl)-2-imidazoline or an acid addition salt thereof is applied.

4. The method of claim 1 in which 2-(2-chloro-3-methylanilinomethyl)-2-imidazoline or an acid addition salt thereof is applied.

5. The method of claim 3 or 4 wherein the pests are ticks.

* * * * *